(12) United States Patent
Sharma et al.

(10) Patent No.: US 7,396,814 B2
(45) Date of Patent: Jul. 8, 2008

(54) METALLOPEPTIDE COMPOSITIONS FOR TREATMENT OF SEXUAL DYSFUNCTION

(75) Inventors: Shubh D. Sharma, Cranbury, NJ (US); Annette M. Shadiack, Somerset, NJ (US); Wei Yang, Edison, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 224 days.

(21) Appl. No.: 11/036,273

(22) Filed: Jan. 14, 2005

(65) Prior Publication Data
US 2005/0164914 A1     Jul. 28, 2005

Related U.S. Application Data

(60) Continuation-in-part of application No. 09/483,837, filed on Jan. 17, 2000, now abandoned, and a continuation-in-part of application No. 10/640,755, filed on Aug. 13, 2003, now Pat. No. 7,307,063, said application No. 09/483,837 is a division of application No. 08/660,697, filed on Jun. 5, 1996, now Pat. No. 6,027,711, which is a continuation-in-part of application No. 08/476,652, filed on Jun. 7, 1995, now Pat. No. 5,891,418, said application No. 10/640,755 is a continuation of application No. PCT/US02/04431, filed on Feb. 13, 2002.

(60) Provisional application No. 60/536,691, filed on Jan. 14, 2004, provisional application No. 60/268,591, filed on Feb. 13, 2001.

(51) Int. Cl.
*A61K 38/16* (2006.01)

(52) U.S. Cl. .............................. 514/6; 514/16; 514/17; 514/492; 530/329; 530/330; 530/331

(58) Field of Classification Search ................. 530/330, 530/331; 514/6, 16, 17, 492
See application file for complete search history.

(56) References Cited

U.S. PATENT DOCUMENTS 5,408,036 A * 4/1995 Ghadiri ...................... 530/304

* cited by examiner

*Primary Examiner*—David Lukton
(74) *Attorney, Agent, or Firm*—Stephen A. Slusher

(57) ABSTRACT

Metallopeptide compositions are provided for treatment of sexual dysfunction in mammals, including male sexual dysfunction, such as erectile dysfunction, and female sexual dysfunction. The metallopeptides include at least one, and preferably two, aromatic amino acid side chain moieties, and are further characterized in that the metallopeptides preferably do not bind or significantly bind to a melanocortin receptor.

12 Claims, No Drawings

SEQUENCE LISTING

<160> NUMBER OF SEQ ID NOS: 1

<210> SEQ ID NO 1
<211> LENGTH: 4
<212> TYPE: PRT
<213> ORGANISM: Artificial
<220> FEATURE:
<223> OTHER INFORMATION: alpha-melanocyte stimulating hormone
      tetrapeptide core sequence

<400> SEQUENCE: 1

His Phe Arg Trp
1

METALLOPEPTIDE COMPOSITIONS FOR TREATMENT OF SEXUAL DYSFUNCTION

CROSS-REFERENCE TO RELATED APPLICATIONS

This application is a continuation-in-part application of U.S. patent application Ser. No. 09/483,837, entitled "Metallopeptide and Metallo-Constructs Combinatorial Libraries and Applications", filed on Jan. 17, 2000, which is a divisional application of U.S. patent application Ser. No. 08/660, 697, entitled "Structurally Determined Metallo-Constructs and Applications", filed on Jun. 5, 1996, and issued as U.S. Pat. No. 6,027,711 on Feb. 2, 2000, which is a continuation-in-part of U.S. patent application Ser. No. 08/476,652, entitled "Peptide-Metal Ion Pharmaceutical Constructs and Applications", filed on Jun. 7, 1995, and issued as U.S. Pat. No. 5,891,418 on Apr. 6, 1999, and the specification of each is incorporated herein by reference. This application is also a continuation-in-part application of U.S. patent application Ser. No. 10/640,755, entitled "Melanocortin Metallopeptides for Treatment of Sexual Dysfunction", filed on Aug. 13, 2003, which is a continuation of International Application Serial No. PCT/US02/04431, entitled "Melanocortin Metallopeptides for Treatment of Sexual Dysfunction", filed on Feb. 13, 2002, which claimed priority to U.S. Provisional Patent Application Ser. No. 60/268,591, entitled "Melanocortin Metallopeptides for Treatment of Sexual Dysfunction", filed on Feb. 13, 2001, and the specification of each is incorporated herein by reference.

This application claims the benefit of the filing of U.S. Provisional Patent Application Ser. No. 60/536,691, entitled "Metallopeptide Compositions for Treatment of Sexual Dysfunction", filed Jan. 14, 2004, and the specification thereof is incorporated herein by reference.

This application is related to application Ser. No. 11/031, 898 entitled "Peptide Compositions for Treatment of Sexual Dysfunction", filed on Jan. 7, 2005, and to application Ser. No. 11/036,281, filed Jan. 14, 2005, entitled "Small Molecule Compositions for Sexual Dysfunction", and the specification thereof of each is incorporated herein by reference.

BACKGROUND OF THE INVENTION

1. Field of the Invention (Technical Field)

The present invention relates to metallopeptide constructs for the treatment of sexual dysfunction in animals, including both male erectile dysfunction and female sexual dysfunction, including methods and formulations for the use and administration of the same.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Sexual dysfunction, including both penile erectile dysfunction or impotence and female sexual dysfunction, are common medical problems. Significant effort has been devoted over the last twenty or more years to develop methods, devices and compounds for treatment of sexual dysfunction. While more effort has been undertaken for treatment of penile erectile dysfunction, female sexual dysfunction is also an area to which significant research and effort has been devoted.

At present, commonly used orally administered drugs for treatment of sexual dysfunction in the male include Viagra®, a brand of sildenafil, Levitra® and Cialis®, all of which are phosphodiesterase 5 (PD-5) inhibitor drugs that increase the persistence of cyclic guanosine monophosphate and thereby enhance erectile response. Another drug approved in Europe for treating male erectile dysfunction is Ixense®, a brand of apomorphin that is a non-selective dopa receptor agonist. Oral and nasal formulations of apomorphin are currently undergoing clinical evaluations in the United States. There are several other medical treatment alternatives currently available depending on the nature and cause of the impotence problem. Some men have abnormally low levels of the male hormone testosterone, and treatment with testosterone injections or pills may be beneficial. However, comparatively few impotent men have low testosterone levels. For many forms of erectile dysfunction, treatment may be undertaken with drugs injected directly into the penis, including drugs such as papaverin, prostaglandin $E_1$, phenoxybenzamine or phentolamine. These all work primarily by dilating the arterial blood vessels and decreasing the venous drainage. Urethral inserts, such as with suppositories containing prostaglandin, may also be employed. In addition, a variety of mechanical aids are employed, including constriction devices and penile implants.

A variety of treatments have also been explored for female sexual dysfunction, including use of sildenafil, although the Food and Drug Administration has not specifically approved such use. Testosterone propionate has also been employed to increase or augment female libido.

A number of other agents have been shown to induce or facilitate penile erection in laboratory animals. These include very diverse classes of ligands such as oxytocin (Benelli A, Poggioli R, Luppi P, Ruini L, Bertolini A, Arletti R., (1994), oxytocin enhances, and oxytocin antagonism decreases, sexual receptivity in intact female rats, *Neuropeptides*: 27:245-50), vasopressin, apomorphin, vasoactive intestinal peptide, melanotropins, and ACTH as well as their analogs.

It is well known to those skilled in art of developing new therapeutic treatments for sexual dysfunction that identification of a new class of therapeutic agents is often achieved by chance. For example, investigations of sildenafil as an agent for treating high blood pressure in humans revealed its effects on facilitating penile erection in men. Similarly, clinical use of apomorphin for treatment of Parkinson's disease uncovered its effects in eliciting penile erections. Human studies on a potent melanotropin agonist as an agent to induce human skin pigmentation established its erectogenic activity. Mainly for this reason, the mechanism by which these ligands elicit a sexual activity response remains largely unknown. Some understanding of the PD-5 class of compounds (e.g. sildenafil) has now been developed. The biological mechanism(s) by which presumably centrally acting molecules, such as oxytocin, vasopressin, apomorphin, vasoactive intestinal peptide, melanotropins and ACTH, elicit a sexual function response is still unclear. That at least a portion of the biological mechanism is central is demonstrated by efficacy following intracerebroventricular (ICV) administration. It is conceivable that all these agents may be interacting at more than one individual receptor site involved in a common downstream biological pathway.

Melanocortin receptor-specific compounds have been explored for use of treatment of sexual dysfunction. In one report, a cyclic α-melanocyte-stimulating hormone ("α-

MSH") analog, called Melanotan-II, was evaluated for erectogenic properties for treatment of men with psychogenic erectile dysfunction. Wessells H. et al., *J Urology* 160:389-393 (1998); see also U.S. Pat. No. 5,576,290, issued Nov. 19, 1996 to M. E. Hadley, entitled Compositions and Methods for the Diagnosis and Treatment of Psychogenic Erectile Dysfunction and U.S. Pat. No. 6,051,555, issued Apr. 18, 2000, also to M. E. Hadley, entitled Stimulating Sexual Response in Females. The peptides used in U.S. Pat. Nos. 5,576,290 and 6,051,555 are also described in U.S. Pat. No. 5,674,839, issued Oct. 7, 1997, to V. J. Hruby, M. E. Hadley and F. Al-Obeidi, entitled Cyclic Analogs of Alpha-MSH Fragments, and in U.S. Pat. No. 5,714,576, issued Feb. 3, 1998, to V. J. Hruby, M. E. Hadley and F. Al-Obeidi, entitled Linear Analogs of Alpha-MSH Fragments. Additional related peptides are disclosed in U.S. Pat. Nos. 5,576,290, 5,674,839, 5,714,576 and 6,051,555. These peptides are described as being useful for both the diagnosis and treatment of psychogenic sexual dysfunction in males and females. These peptides are related to the structure of melanocortins. A preferred melanocortin receptor agonist is Ac-Nle-cyclo(-Asp-His-D-Phe-Arg-Trp-Lys)-OH, called PT-141, as disclosed in U.S. Pat. No. 6,579,968, incorporated herein by reference. It is believed that melanocortin agonists, including PT-141, amplify the release of nitric oxide released from nitrergic nerve fibers, and the cavernosal nerve in particular, enhancing erectile response by enhancing normal central and peripheral reflex pathways.

Metallopeptides are taught for treatment of sexual dysfunction, as disclosed in commonly owned application PCT/US02/04431, Melanocortin Metallopeptides for Treatment of Sexual Dysfunction, filed Feb. 13, 2002, and incorporated herein by reference in its entirety. However, these metallopeptides display specific interaction (binding, and agonism or antagonism) with one or more melanocortin receptors, in addition to being useful for treatment of sexual dysfunction.

It has long been believed that male and female sexual response to melanocortin receptor-related compounds was related to the central tetrapeptide sequence, His$^6$-Phe$^7$-Arg$^8$-Trp$^9$ (SEQ ID NO:1) of native α-MSH. In general, all melanocortin peptides share the same active core sequence, His-Phe-Arg-Trp (SEQ ID NO:1), including melanotropin neuropeptides and adrenocorticotropin. Melanocortin-3 receptor (MC3-R) has the highest expression in the arcuate nucleus of the hypothalamus, while melanocortin-4 receptor (MC4-R) is more widely expressed in the thalamus, hypothalamus and hippocampus. A central nervous system mechanism for melanocortins in the induction of penile erection has been suggested by experiments demonstrating penile erection resulting from ICV administration of melanocortins in rats. While the mechanism of His-Phe-Arg-Trp (SEQ ID NO:1) induction of erectile response has never been fully elucidated, it has been generally accepted that the response involves the central nervous system, and binding to MC3-R and/or MC4-R, and according to most researchers, MC4-R.

A number of peptides and constructs have been proposed which are ligands that alter or regulate the activity of one or more melanocortin receptors. For example, International Patent Application No. PCT/US99/09216, entitled Isoquinoline Compound Melanocortin Receptor Ligands and Methods of Using Same, discloses two compounds that induce penile erections in rats. However, these compounds were administered by injection at doses of 1.8 mg/kg and 3.6 mg/kg, respectively, and at least one compound resulted in observable side effects, including yawning and stretching. Other melanocortin receptor-specific compounds with claimed application for treatment of sexual dysfunction are disclosed in International Patent Application No. PCT/US99/13252, entitled Spiropiperidine Derivatives as Melanocortin Receptor Agonists. International Patent Application Nos. PCT/US00/14930, PCT/US00/19408, WO 01/05401, WO/00/53148, WO 01/00224, WO 00/74679, WO 01/10842 and the like disclose other compounds that may be so utilized.

Most of investigators in this field ascribe the sexual activity of melanotropin ligands to MC4-R. For example, see Van der Ploeg L H, Martin W J, Howard A D, Nargund R P, Austin C P, Guan X, Drisko J, Cashen D, Sebhat I, Patchett A A, Figueroa D J, DiLella A G, Connolly B M, Weinberg D H, Tan C P, Palyha O C, Pong S S, MacNeil T, Rosenblum C, Vongs A, Tang R, Yu H, Sailer A W, Fong T M, Huang C, Tota M R, Chang R S, Stearns R, Tamvakopoulos C, Christ G, Drazen D L, Spar B D, Nelson R J, Macintyre D E. A role for the melanocortin 4 receptor in sexual function. *Proc Natl Acad Sci USA*. 99:11381-6 (2002). Evidence in favor of this hypothesis comes from the fact that a sexual response elicited by an MC4-R agonist can be blocked by an MC4-R antagonist. However, a few reports also suggest that MC4-R receptors may not be involved in eliciting sexual function response (Vergoni A V, Bertolini A, Guidetti G, Karefilakis V, Filaferro M, Wikberg J E, Schioth H B. Chronic melanocortin 4 receptor blockage causes obesity without influencing sexual behavior in male rats. *J Endocrinol*, 166:419-26 (2000)).

Because of the myriad biological effects of compounds specific for melanocortin receptors, there is a need for compounds and methods, including methods of selection of compounds, to differentiate the effects. More specifically, there is a need for compounds that effect a sexual response, by the same or similar regulatory pathways as those implicated in MC4-R-specific compounds, without eliciting other biological effects related to MC4-R, including without limitation energy homeostasis or feeding behaviors. For most pharmaceutical applications it is desirably to have a compound that is specific for a single biological effect, such as for example a compound that regulates and elicits a sexual response, and that is not substantially specific for MC4-R, is not an agonist or antagonist with respect to MC4-R, and that does not regulate energy homeostasis, such as by decreasing food intake and/or body weight.

BRIEF SUMMARY OF THE INVENTION

The invention relates to metallopeptide constructs that are characterized in that they do not bind, or significantly bind, MC4-R, or any other known melanocortin receptor, but which have some structural similarities to at least one molecular region of melanocortin receptor binding peptide agents, and which further elicit a sexual response in mammals, including inducing an erectile response in males. Thus the invention relates to metallopeptides containing a Phe-Arg or related D-Phe-Arg sequence, or structural mimic or homolog thereof, similar to that in melanocortin receptor-specific peptides or metallopeptides, but that do not bind or substantially bind to any melanocortin receptor. The metallopeptides containing a D-Phe-Arg sequence induce erectile responses similar to agents described in prior art that bind MC4-R. In another embodiment, the invention relates to metallopeptides containing a His-D-Phe-Arg sequence, or structural mimic or homolog thereof, but specifically not containing a Trp residue or mimic or homolog thereof, as in a His-D-Phe-Arg-Trp sequence, such that the resulting metallopeptide does not bind, or substantially bind, to any melanocortin receptor. The metallopeptides of the invention containing a D-Phe-Arg sequence or His-D-Phe-Arg sequence, or structural mimic or homolog thereof, elicit a sexual response in mammals, including inducing an erectile response in males.

In another embodiment, the invention relates to metallopeptides which are melanocortin receptor-specific antagonists, but which nonetheless induce an erectile response in males.

The invention also includes pharmaceutical compositions of matter, including a metallopeptide of this invention and a pharmaceutically acceptable carrier.

The metallopeptides of this invention, and pharmaceutical compositions of this invention, may be used for stimulating sexual response in a mammal. The invention thus also includes a method for stimulating sexual response in a mammal, in which a pharmaceutically sufficient amount of a composition is administered. The mammal may be male or female. In this method, the composition can also include a pharmaceutically acceptable carrier. The metallopeptide or pharmaceutical composition may be administered by any means known in the art, including administration by injection, administration through mucous membranes, buccal administration, oral administration, dermal administration, inhalation administration and nasal administration. In a preferred embodiment, administration is by oral administration of a specified amount of a formulation including an appropriate carrier, bulking agent and the like.

A primary object of the present invention is a pharmaceutical for use in treatment of sexual dysfunction that is not melanocortin receptor-specific.

A second object is to provide a metallopeptide-based pharmaceutical for use in treatment of male sexual dysfunction, including erectile dysfunction, which is not melanocortin receptor-specific.

Yet another object is to provide a metallopeptide-based pharmaceutical for use in treatment of female sexual dysfunction that is not melanocortin receptor-specific.

Yet another object is to provide a metallopeptide-based pharmaceutical for use in treatment of sexual dysfunction which, to the extent it is specific for any melanocortin receptor, is an antagonist of such receptor, and not an agonist.

An advantage of the present invention is that it provides a metallopeptide-based pharmaceutical for use in treatment of sexual dysfunction which may be administered by delivery systems other than art conventional intravenous, subcutaneous or intramuscular injection, including but not limited to oral delivery systems, nasal delivery systems and mucous membrane delivery systems.

Other objects, advantages and novel features, and further scope of applicability of the present invention will be set forth in part in the detailed description to follow, and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE INVENTION

Definitions. Before proceeding further with the description of the invention, certain terms are defined as set forth herein.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N- or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. For the most part, the peptides of this invention comprise fewer than 20 amino acids, and preferably fewer than 10 amino acids, and most preferably ranging from about 3 to 7 amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The "amino acids" used in this invention, and the term as used in the specification and claims, include the known naturally occurring protein amino acids, which are referred to by both their common three letter abbreviation and single letter abbreviation. See generally *Synthetic Peptides: A User's Guide*, G. A. Grant, ed., W.H. Freeman & Co., New York (1992), the teachings of which are incorporated herein by reference, including the text and table set forth at pages 11 through 24. As discussed above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference. In addition, the following abbreviations of amino acids and compounds used in making or describing amino acids have the meanings giving:

Aminoheptanoyl —$NH_2$—$(CH_2)_6CO$—
Arg(Tos)—$N^G$-para-tosyl-arginine
Arg($NO_2$)—$N^G$-nitro-arginine
Arg(Pbf)—$N^G$-2,2,4,6,7-pentamethydihydrobenzofuran-5-sulfonyl-arginine
Arg(Mtr)—$N^G$-4-methoxy-2,3,6-trimethylbenzenesulfonyl-arginine
Arg(Me)—$N^G$-methyl-arginine
Arg(Pmc)—$N^G$-2,2,5,7,8-pentamethylchroman-6-sulonyl-arginine
D/L Atc—(D,L)-2-aminotetralin-2-carboxylic acid
11-Aun—11-amino undecanoic acid
AVA—5-amino valeric acid
Bip—biphenylalanine
Bz—benzoyl
Cha—cyclohexylalanine
Chg—cyclohexylglycine
Cit—citrulline
Dip—3,3-Diphenylalanine Et—ethyl
Hphe—homophenylalanine
Lys(Z)—N-epsilon-benzyloxycarbonyl-lysine
Me—methyl
NaI 1—3-(1-naphthyl)alanine
NaI 2—3-(2-naphthyl)alanine
(N-Bzl)NaI 2—N-benzyl-3-(2-naphthyl) alanine
(N-PhEt)NaI 2—N(2-phenylethyl)-3-(2-naphthyl) alanine
Phg—phenylglycine
pF-Phe—para-fluoro-phenylalanine
Phe(4-Br)—4-bromo-phenylalanine
Phe(4-$CF_3$)—4-trifluoromethyl-phenylalanine
Phe(4-Cl)—4-chloro-phenylalanine
Phe(2-Cl)—2-chloro-phenylalanine
Phe(2,4-diCl)—2,4,-dichloro-phenylalanine
Phe(3,4-diCl)—3,4,-dichloro-phenylalanine
Phe(3,4-diF)—3,4,-difluoro-phenylalanine
Phe(4-I)—4-iodo-phenylalanine
Phe(3,4-di-OMe)—3,4,-dimethoxy-phenylalanine
Phe(4-Me)—4-methyl-phenylalanine
Phe(4-$NO_2$)—4-nitro-phenylalanine
Qal(2')—beta-(2-quinolyl)-alanine
Sal—3-styrylalanine
TFA—trifluoroacetyl
Tic—1,2,3,4-tetrahydroisoquinoline-3-carboxylic acid
Tle—tert-butylalanine
Tyr(Bzl)—O-benzyl-tyrosine
Tyr(BzlDiCl 2,6)—O-(2,6 dichloro)benzyl-tyrosine
Ser(Bzl)—O-benzyl-serine In the listing of compounds according to the present invention, conventional amino acid residues have their conventional meaning as given in Chapter 2400 of the *Manual of Patent Examining Procedure*, 8$^{th}$ Ed. Thus, "Cys" is cysteine; "His" is histidine; "D-Phe" is D-phenylalanine; "Arg" is arginine; "Trp" is tryptophan; "Lys" is lysine; and so on.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue".

The term "amino acid side chain moiety" used in this invention includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. An amino acid side chain moiety further includes a derivative of an amino acid side chain moiety, as "derivative" is defined herein.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties. Derivatives of amino acid side chain moieties further include amino acid side chain moieties, preferably amino acid side chain moieties with a functional group, the amino acid side chain moieties further including one or more protecting groups, preferably an orthogonal protecting group.

In the specification and the claims, the term "homolog" includes, without limitation, (a) a D-amino acid residue or side chain substituted for an L-amino acid residue side chain, (b) a post-translationally modified residue or side chain substituted for the residue or side chain in a parent polypeptide, (c) a non-protein or other modified amino acid residue or side chain based on such residue or side chain in a parent polypeptide, such as phenylglycine, homophenylalanine, ring-substituted halogenated, and alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monovalent or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH$_2$), such as methylamide, ethylamide, propylamide, and the like.

An "imide" includes compounds containing an imido group (—CO.NH.CO—).

An "amine" includes compounds that contain an amino group (—NH$_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

The term "halogen" is intended to include the halogen atoms fluorine, chlorine, bromine and iodine, and groups including one or more halogen atoms, such as —CF$_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound or peptide of the present invention and a pharmaceutically acceptable carrier.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

The peptides disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the peptides of this invention may be synthesized by solid-phase synthesis and purified according to methods known in the art. Any of a number of well-known procedures utilizing a variety of resins and reagents may be used to prepare the compounds of this invention.

The peptides of this invention may be in the form of any pharmaceutically acceptable salt. Acid addition salts of the compounds of this invention are prepared in a suitable solvent from the peptide and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The invention provides a pharmaceutical composition that includes a metallopeptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

Routes of Administration. If it is administered by injection, the injection may be intravenous, subcutaneous, intramuscular, intraperitoneal or other means known in the art. The metallopeptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

The metallopeptides of this invention may be formulated or compounded into pharmaceutical compositions that include at least one metallopeptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of metallopeptides of this invention administered to a patient will vary between fairly wide ranges depending upon the mode of administration, the formulation used, and the response desired.

In general, the metallopeptide compounds of this invention may be synthesized by solid-phase synthesis and purified according to methods known in the art. Any of a number of well-known procedures utilizing a variety of resins and reagents may be used to prepare the compounds of this invention. The peptides may be complexed with a metal ion, such as a rhenium ion, as hereafter described.

The metallopeptide compounds of this invention may also be used for diagnostic purposes, such as to diagnose causes of erectile dysfunction in males, or sexual dysfunction in mammals generally. Thus, the metallopeptide compounds maybe administered and the erectile reaction of the patient monitored. The receptor or enzyme for which the peptide compounds of this invention are specific, when such receptor or enzyme is identified, may similarly be directly measured, such as in blood or other patient samples.

Combination Therapy. It is also possible and contemplated to use the metallopeptides of this invention in combination with other drugs or agents. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, metallopeptides of the invention are used in combination with a therapeutically effective amount of a cyclic-GMP-specific phosphodiesterase inhibitor or an alpha-adrenergic receptor antagonist. Similarly, the metallopeptides of this invention may be used in combination with any known mechanical aids or devices.

The present invention thus provides methods of treating sexual dysfunction, the methods comprising the step of administering to the patient having or at risk of having sexual dysfunction a therapeutically effective amount of a metallopeptide of this invention in combination with a therapeutically effective amount of a second sexual dysfunction pharmaceutical agent. The metallopeptide of this invention may be administered simultaneously with, prior to or subsequent to administration with a therapeutically effective amount of a second sexual dysfunction pharmaceutical agent. Preferably the metallopeptide of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the metallopeptide of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the metallopeptide of this invention when desired or needed by the patient.

The present invention thus provides methods of treating sexual dysfunction, the methods comprising the step of administering to a patient having or at risk of having sexual dysfunction a therapeutically effective amount of a metallopeptide of this invention in combination with a compound that is a melanocortin receptor agonist.

The present invention further also provides methods of treating sexual dysfunction, the methods comprising the step of administering to a patient having or at risk of having sexual dysfunction a therapeutically effective amount of a metallopeptide of this invention in combination with a compound that is a melanocortin receptor agonist and in combination with another compound that is useful in the treatment of sexual dysfunction.

In a preferred embodiment of combination therapy the sexual dysfunction is female sexual dysfunction.

In an especially preferred embodiment of combination therapy the sexual dysfunction is erectile dysfunction.

In a preferred embodiment of the foregoing methods, the melanocortin receptor agonist is an agonist of MC3-R or MC4-R, and preferably MC4-R. The agonist may be a non-selective MC3-R and MC4-R agonist.

The present invention also provides pharmaceutical compositions that comprise 1) a metallopeptide of this invention and 2) a compound that is a melanocortin receptor agonist.

The present invention also provides pharmaceutical compositions that comprise 1) a metallopeptide of this invention; 2) a compound that is a melanocortin receptor agonist; and 3) a third compound useful for the treatment of sexual dysfunction.

The present invention also provides pharmaceutical compositions that comprise 1) a metallopeptide of this invention and 2) a second compound useful for the treatment of sexual dysfunction.

Representative agonists of the melanocortin receptor which are a second compound useful in combination therapy are disclosed in the following publications, which are incorporated here by reference in their entirety: M. E. Hadley et al., Discovery and development of the novel melanogenic drugs, in *Integration of Pharmaceutical Discovery and Development: Case Studies*, edited by Borschart et al., Plenum Press, New York (1998); R. T. Dorr et al., Evaluation of Melanotan-II, A Superpotent Cyclic Melanotropic Peptide in a Pilot Phase-I Clinical Study. Life Sci. 58:1777-1784 (1996); and R. A. H. Adan, Identification of Antagonists for Melanocortin MC3, MC4, and MC5 Receptors. *Eur. J. Pharmacol.*, 269: 331-337 (1994).

In one embodiment of the composition above, the agonists are melanocyte-stimulating hormones (MSH) including α-, β-, and γ-MSH and/or adrenocorticotropic hormones (ACTH).

In another embodiment of the composition above, the melanocortin receptor agonist is Melanotan-II (MT-II). A preferred melanocortin receptor agonist includes any linear or cyclic melanocortin receptor-specific agonist peptide disclosed in International Application WO 03/006620 or a metallopeptide disclosed in International Application WO 02/064091. A particularly preferred melanocortin receptor agonist is Ac-Nle-cyclo(-Asp-His-D-Phe-Arg-Trp-Lys)-OH, as disclosed in U.S. Pat. No. 6,579,968. Alternatively, the agonist may be any agonist disclosed in any of the following patents or patent applications: U.S. Pat. Nos. 6,534,503, 6,472,398, 6,458,790, 6,410,548, 6,376,509, or 6,350,760; U.S. Published Application Nos. 2002/0137664, 2002/0004512, 2002/0143141, or U.S. 2003/0069169; or International Application No. WO 02/18437. The agonist of the melanocortin receptor may preferably be selective for MC4-R.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; α-adrenergic antagonists; dopanergic ligands; androgens; selective androgen receptor modulators (SARMs); buproprion; vasoactive intestinal peptide (VIP); neutral endopeptidase inhibitors (NEP); neuropeptide Y receptor antagonists (NPY); and bombesin receptor-3 antagonists.

In an embodiment of the method and composition, the second sexual dysfunction pharmaceutical agent is testosterone.

In another embodiment of combination therapy, the second sexual dysfunction pharmaceutical agent is a type V phosphodiesterase inhibitor (PDE-5). For example, the PDE-5 inhibitor may be Viagra®, a brand of sildenafil, Levitra®, Cialis®, or may be 1-[[3-(6,7-dihydro-1-methyl-7-oxo-3-propyl-1-H-pyrazolo[4,3-d]pyrimidin-5-yl]-4-ethoxy-phenyl]sufonyl)-4-methylpiperazine citrate salt, as disclosed in U.S. Published Application No. 2003/0083228.

In another embodiment of the composition above, the compound useful for the treatment of sexual dysfunction is an estrogen agonist/antagonist. In one embodiment, the estrogen agonist/antagonist is (−)-cis-6-phenyl-5-[-4-(2-pyrrolidin-1-yl-ethoxy)-phenyl]-5,6,7,8-tetrahydro-napth-thalene-2-ol (also known as lasofoxifene) or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, 6-(4-hydroxy-phenyl)-5-[4-(2-piperidine-1-yl-ethoxy)-benzyl]-napthalen-2-ol, {4-[2-(2-aza-bicyclo[2.2.1]hept-2-yl)-ethoxy]-phenyl}-[6-hydroxy-2-(4-hydroxy-phenyl)-benzo[b]thiopehn-3-yl]-methanone, EM-652, EM-800, GW 5368, GW 7604, TSE-424 and optical or geometric isomers thereof; and pharmaceutically acceptable salts, N-oxides, esters, quaternary ammonium salts, and prodrugs thereof.

In yet another embodiment, a metallopeptide of this invention may be used in combination with any known mechanical aids or devices.

The present invention also provides kits for the treatment of sexual dysfunction (including erectile dysfunction), the kits comprising: a first pharmaceutical composition including a metallopeptide of this invention; a second pharmaceutical composition comprising a second compound useful for the treatment of sexual dysfunction; and, a container for the first and second compositions.

Female Sexual Dysfunction. The metallopeptide compounds of this invention may be used to treat female sexual dysfunction as well as male sexual dysfunction. In general, the dosing schedules and doses for females are comparable to those for males.

The metallopeptide compounds of this invention, in that they are not specific for any heretofore known melanocortin receptor, may thereby define a new class of receptor, which receptor may be a protein receptor or may be an enzyme-associated receptor. The invention thus includes other compounds and structures that are functionally equivalent to the peptide compounds of this invention. These other compounds are similarly characterized as effective in inducting erectile activity, preferably at very low doses, without being specific for any known melanocortin receptor.

In yet another embodiment, this invention provides metallopeptide compounds that bind to MC4-R and are antagonists, but that nonetheless induce erectile activity, and may thus be used in treatment of sexual dysfunction. The invention thus provides alternative pathways to treatment of sexual dysfunction not addressed by other modalities, including A-MSH analogs or agonists.

General Structures of the Invention. In one embodiment, the compositions according to this invention include small linear peptides composed of "L" and "D" amino acids, as shown hereafter in Formulas I to VII. Peptides of any of Formulas I through III below are complexed with a metal ion to form a metallopeptide, wherein a W residue and at least one Xaa residue are complexed with ReO[V], or alternatively another tetradentate metal ion, including but not limited to technetium. Complexation of peptides with rhenium, including specifically peptides of this invention, is taught in International Patent Application Serial No. PCT/US00/16396, Melanocortin Receptor-Specific Metallopeptide Constructs, Combinatorial Libraries and Applications, filed on Jun. 14, 2000; International Patent Application Serial No. PCT/US99/29743, entitled Metallopeptide Combinatorial Libraries and Applications, filed Dec. 14, 1999; U.S. Pat. No. 6,027,711 entitled Structurally Determined Metallo-Constructs and Applications, issued Feb. 22, 2000; and U.S. Pat. No. 5,891,418 entitled Peptide—Metal Ion Pharmaceutical Constructs and Applications, issued Apr. 6, 1999, the teachings of all of which are incorporated herein by reference as if set forth in full. The invention thus provides a pharmaceutical composition for treating sexual dysfunction in a mammal which comprises a peptide or a pharmaceutically acceptable salt thereof, complexed to a metal ion and thereby forming a metallopeptide, the peptide being of formula I, II or III:

$$Y\text{-}Xaa_1\text{-}Xaa_2\text{-}W\text{-}Z \quad \text{I}$$

$$Y\text{-}Xaa_1\text{-}W\text{-}Xaa_2\text{-}Z \quad \text{II}$$

$$Y\text{-}W\text{-}Xaa_1\text{-}Xaa_2\text{-}Z \quad \text{III}$$

wherein:
Y is H, an acyl group with a linear or branched $C_1$ to $C_{17}$ alkyl, aryl, heteroaryl, alkene, alkenyl or aralkyl chain including an $NH_2$, $NH_3^+$, or NH group or a corresponding acylated derivative, or is an amino acid, a dipeptide or a tripeptide, with the side chains thereof independently selected from H or a linear or branched $C_1$ to $C_{17}$ alkyl, aryl, heteroaryl, alkene, alkenyl or aralkyl chain, with an N-terminus $NH_2$, $NH_3^+$, NH group or a corresponding acylated derivative;

$Xaa_1$ and $Xaa_2$ are independently each an L- or D-amino acid with a side chain containing a $C_1$ to $C_6$ aliphatic linear or branched chain or an L- or D-amino acid with a side chain containing at least one aromatic moiety, on the proviso that at least one of $Xaa_1$ and $Xaa_2$ is an L- or D-amino acid with a side chain containing at least one aromatic moiety;

Z is —OH, $NH_2$, NH—R, or is an amino acid with a side chain selected from H, a $C_1$ to $C_6$ aliphatic amino acid side chain moiety or a neutral hydrogen bonding or positively charged amino acid side chain moiety, with a C-terminus —OH, $NH_2$, or NH—R;

W is an L- or D-amino acid with a side chain containing at least one reactive sulfur (S) atom; and R is an aliphatic $C_1$ to $C_{17}$ chain.

In one preferred embodiment, in the pharmaceutical composition $Xaa_1$ and $Xaa_2$ are each independently an L- or D-amino acid with a side chain containing at least one aromatic moiety.

In a preferred embodiment, the peptide of the pharmaceutical composition does not inhibit or significantly the binding of α-MSH or an α-MSH analog to melanocortin receptors. Thus the peptide does not inhibit or significantly inhibit the binding of α-MSH or an α-MSH analog to MC4-R, and further does not inhibit or significantly inhibit the binding of α-MSH or an α-MSH analog to MC3-R. In general, the peptide is not a melanocortin receptor agonist, and is preferably not an MC4-R agonist or an MC3-R agonist.

In one embodiment, $Xaa_1$ is Ser(Bzl) or comprises Phe or NaI. Where $Xaa_1$ comprises Phe, Phe can be an L- or D-isomer of Phe, pF-Phe, Phe(4-Br), Phe(4-$CF_3$), Phe(4-Cl), Phe(2-Cl), Phe(2,4-diCl), Phe(3,4-diCl), Phe(3,4-diF), Phe(4-I), Phe(3,4-di-OMe), Phe(4-Me), or Phe(4-$NO_2$). Where $Xaa_1$ comprises NaI, NaI can be an L- or D-isomer of NaI, NaI 1 or NaI 2. It is also possible and contemplated that $Xaa_2$ comprises Phe or NaI. In this embodiment, Phe can be an L- or D-isomer of Phe, pF-Phe, Phe(4-Br), Phe(4-$CF_3$), Phe(4-Cl), Phe(2-Cl), Phe(2,4-diCl), Phe(3,4-diCl), Phe(3,4-diF), Phe (4-I), Phe(3,4-di-OMe), Phe(4-Me), or Phe(4-$NO_2$) and NaI can be an L- or D-isomer of NaI, NaI 1 or NaI 2.

In another embodiment, $Xaa_1$ is an L- or D-isomer of Ala or $Xaa_2$ is an L- or D-isomer of Ala. Alternatively, $Xaa_1$ or $Xaa_2$ can include at least one aromatic moiety functionalized with at least one halogen, alkyl group or aryl group.

Y can be aminoheptanoyl, and can include an acyl group, including but not limited to an acetyl group.

Z can include Arg, including an L- or D-isomer of Arg, Arg($NO_2$), Arg(Tos), Arg(Pbf), Arg(Mtr), Arg(Me), or Arg (Pmc). Z can alternatively include an L- or D-isomer of Cit, Lys or Orn.

W is preferably an L- or D-3-mercapto amino acid, including but not limited to L- or D-cysteine, L- or D-penicillamine, 3-mercapto phenylalanine, or a derivative of any of the foregoing.

In a preferred embodiment, there is no Trp residue or homolog of a Trp residue in the peptide for formula I, II or III. The metallopeptides of formula I, II or III can thus be characterized in that they include amino acid side chain moieties the same as, homologs of or corresponding to side chains of His, Phe and Arg, but specifically omit an amino acid side chain moiety the same as, a homolog of or corresponding to Trp.

The metallopeptides of this invention can form a constituent part of a pharmaceutical composition further including a second sexual dysfunction pharmaceutical agent. In one embodiment, the second sexual dysfunction pharmaceutical agent is an MC4-R agonist. A preferred MC4-R agonist is Ac-Nle-cyc/o(Asp-His-D-Phe-Arg-Trp-Lys)-OH. In another embodiment, the second sexual dysfunction pharmaceutical agent is a PDE-5 inhibitor. A preferred PDE-5 inhibitor is sildenafil. In yet another embodiment, the second sexual dysfunction pharmaceutical agent is testosterone. In yet another embodiment, the second sexual dysfunction pharmaceutical agent is an estrogen agonist/antagonist.

In an alternative embodiment, the invention can be characterized as a peptide of formula IV, V, VI or VII:

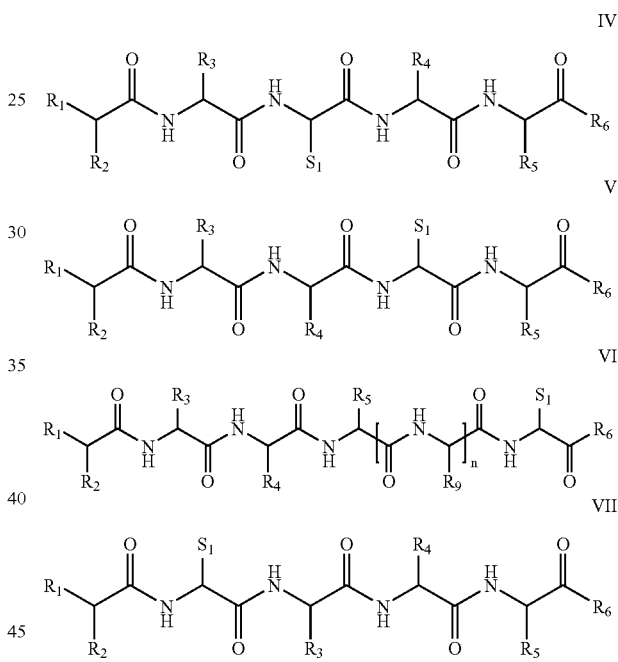

wherein the peptide is complexed with a metal ion, preferably a rhenium ion.

In peptides of formula IV, V, VI or VII, $R_1$ is $NH_2$, $NH_3^+$, $NH_2$—$R_7$, $R_8$—$NH_2$ or H. $R_2$ is H or a linear or branched $C_1$ to $C_{17}$ alkyl, aryl, heteroaryl, alkene, alkenyl, or aralkyl chain. $R_2$ may thus include a $C_1$ to $C_{17}$ aliphatic linear or branched chain, an omega amino derivative of a $C_1$ to $C_{17}$ aliphatic linear or branched chain, or an acylated derivative of an omega amino derivative of a $C_1$ to $C_{17}$ aliphatic linear or branched chain.

$R_3$ and $R_4$ are independently a $C_1$ to $C_6$ aliphatic linear or branched chain, including $CH_3$, or an aromatic amino acid side chain moiety, on the proviso that not more than one of $R_3$ and $R_4$ is a $C_1$ to $C_6$ aliphatic linear or branched chain. In a preferred embodiment, both $R_3$ and $R_4$ are aromatic amino acid side chain moieties. Optionally the aromatic amino acid side chain moiety is derived from a natural or synthetic L- or D-amino acid, and is an aromatic substituted aryl or heteroaryl side chain. The aromatic ring or rings of the amino acid side chain moiety may be functionalized with one or more halogens or one or more alkyl or aryl groups. The aromatic amino acid side chain moiety is preferably selected from the following:
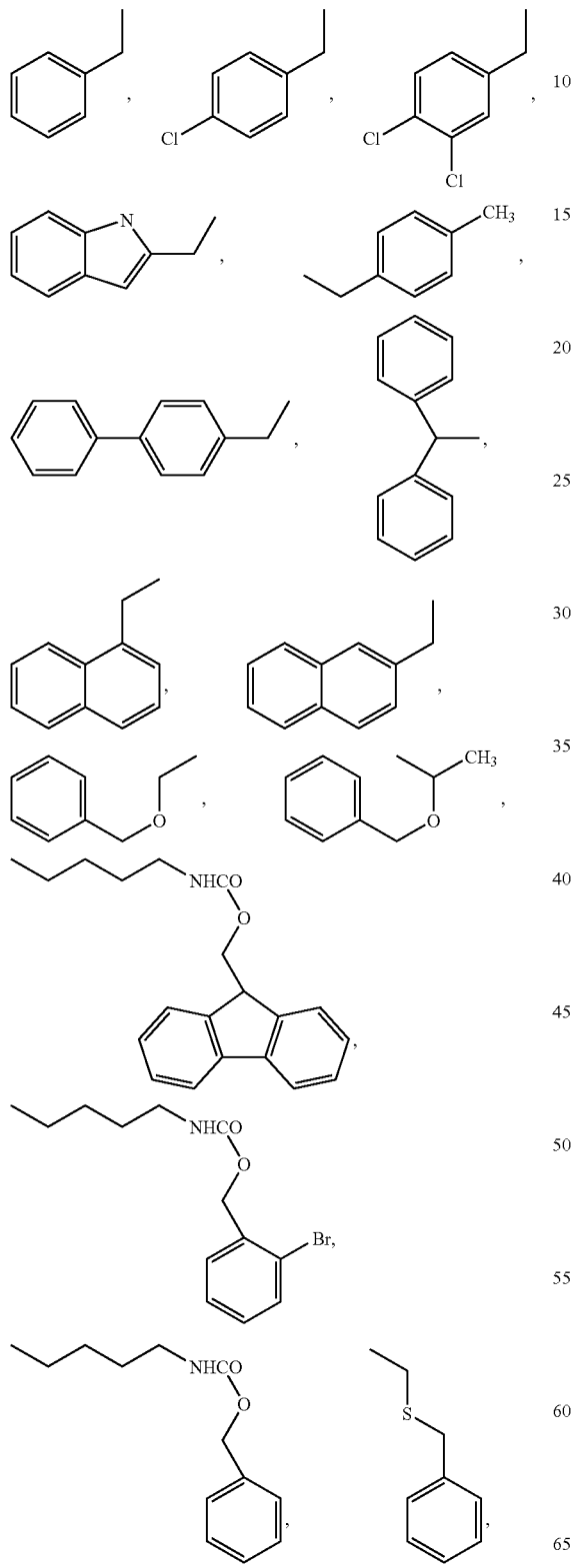
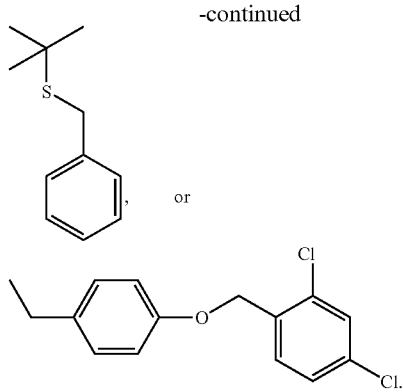
Alternatively, the aromatic amino acid side chain moiety $R_3$ or $R_4$, or independently $R_3$ and $R_4$, can be selected from the following:
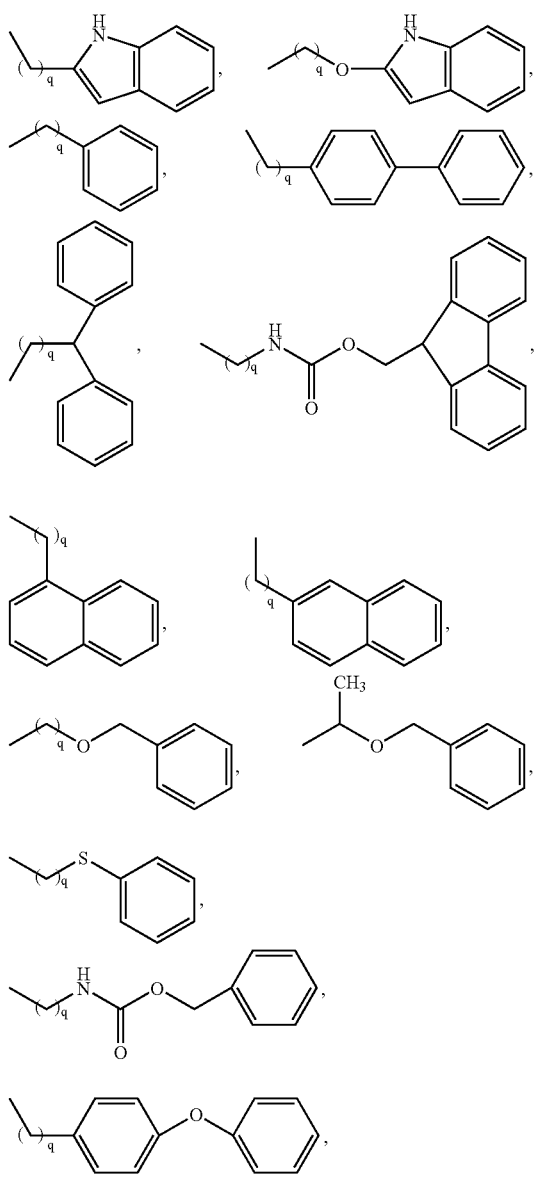

-continued

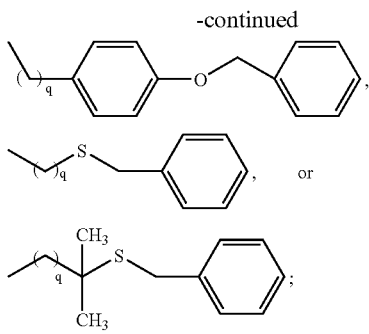

wherein q is from 0 to 5, and any aromatic ring is optionally functionalized with one or more halogen, alkyl or aryl groups.

$R_5$ is a $C_1$ to $C_6$ linear or branched chain or a neutral hydrogen bonding or positively charged amino acid side chain moiety. Optionally the $C_1$ to $C_6$ linear or branched chain is $CH_3$. Optionally the neutral hydrogen bonding or positively charged amino acid side chain moiety is an aliphatic or aromatic amino acid side chain moiety derived from a natural or synthetic L- or D-amino acid, wherein the moiety includes at least one nitrogen-containing group, including an amide, imide, amine, guanidine, urea, urethane, or nitrile. The $R_5$ nitrogen-containing amino acid side chain moiety is preferably selected from the following:

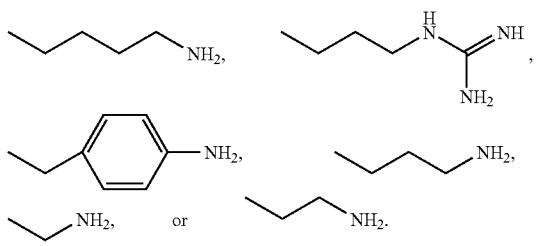

The $R_5$ neutral aliphatic amino acid side chain moiety, wherein the side chain includes hydrogen donors and/or acceptors, is preferably selected from the following:

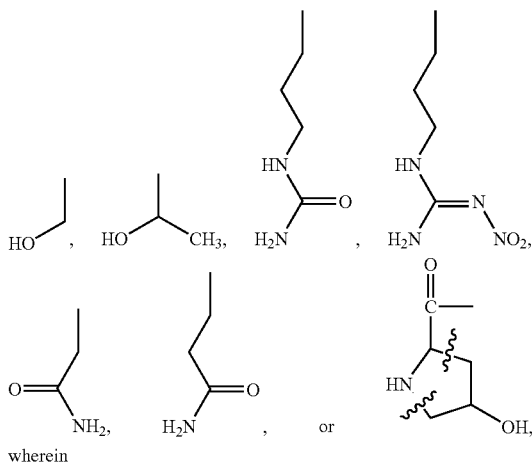

wherein

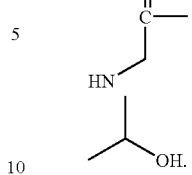

is a portion of the backbone, and $R_5$ is $R_6$ is OH, $NH_2$, or NH—$R_7$.

$R_7$ is from 1 to 3 amino acid residues or a $C_1$-$C_{17}$ chain, including an alkyl, aryl, heteroaryl, alkene, alkenyl, or aralkyl.

$R_8$ is an amino acid residue with an aliphatic side chain or its corresponding N-acylated derivative.

$R_9$ is H or $CH_3$.

The index value n is 0, in which case it is not present, or is 1.

$S_1$ is an amino acid side chain moiety including a sulfur atom (S) for metal ion complexation. Preferred amino acid side chain moieties include the side chain of L- or D-configurations of Cys, Pen and Hcys. The N-terminal side adjacent alpha amino nitrogen atom (N) is further preferably employed in metal ion complexation.

In compounds of Formulas IV, V, VI or VII, the peptides are complexed with a metal ion, such as Rhenium (Re), thereby resulting in a metallopeptide. In a preferred embodiment, an $N_3 S_1$ ligand is formed with the coordination sphere of an ReO(V) ion. In the metallopeptides resulting from metal ion complexation of peptides of formulas V and VI, both the S of $S_1$ and the three immediately preceding alpha amino N atoms contribute to metal ion complexation, thereby forming the $N_3S_1$ ligand. In the metallopeptide resulting from complexation of a peptide of formula IV, the $N_3S_1$ ligand is likewise formed when $R_1$ is $NH_2$.

Melanocortin Receptor Binding Assays. The metallopeptides of the invention are characterized, in part, in that they do not inhibit, or do not substantially inhibit, the binding of α-MSH or an α-MSH analog to melanocortin receptors, and specifically MC1-R, MC3-R, MC4-R or MC5-R, such as by means of a competitive inhibition binding assay, as defined herein. Thus at a 1 μM concentration the metallopeptide does not inhibit the binding of α-MSH or an α-MSH analog to MC4-R. NDP-MSH is one example of an α-MSH analog. Similarly, at a 1 μM concentration the metallopeptide does not inhibit the binding of α-MSH or an α-MSH analog to MC3-R. The metallopeptide is further not a melanocortin receptor agonist, and is specifically not a MC4-R agonist or a MC3-R agonist.

A competitive inhibition binding assay was conducted using membranes prepared from hMC3-R, hMC4-R, hMC5-R, and B-16 mouse melanoma cells (containing MC1-R) using 0.4 nM $^{125}$I-NDP-MSH (0.2 nM for MC1-R) (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the metallopeptides of this invention, at a 1 μM concentration, for determining inhibition of the binding of $^{125}$I-NDP-MSH to its receptor. Non-specific binding was measured by complete inhibition of binding of $^{125}$I-NDP-MSH in the assay in the presence of 1 μM α-MSH. Incubation was for 90 minutes at 37° C., after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 μM α-MSH. The cpm obtained in the presence of metallopeptides of this invention were normalized with respect to 100% specific binding to determine the percent inhibition of $^{125}$I-NDP-MSH binding. Each assay was conducted in triplicate.

A metallopeptide did not "inhibit" α-MSH binding, determined by inhibition of binding of $^{125}$I-NDP-MSH at a 1 μM concentration, when the measured percent inhibition was less than 10%, and preferably when no inhibition was detectable (the measured percent inhibition was 0% or less). A metallopeptide did not "substantially bind" to a melanocortin receptor, and did not "substantially inhibit" α-MSH binding, when at a 1 μM concentration the measured percent inhibition was less than about 40%.

Functional assays to determine agonist or antagonist status of a metallopeptide may be conducted by any means known in the art. In one method, a cAMP assay is performed. Cells transfected with human MC4-R are grown to confluence in 96 well plates (plating approximately 250,000 cells per well). Identical sets of cells in triplicate are treated with 0.2 mM isobutylmethylxanthine (IBMX) and the chosen concentration of the metallopeptide or alternatively the metallopeptide in the presence of 20 nM NDP-MSH. Cells similarly treated but with only 20 nM NDP-MSH serve as positive control in a volume of 200 μL. A buffer blank, as a negative control, is also included. Incubation is for one hour at 37° C. after which the cells are lysed by the addition of 50 μL of a cell lysis buffer. Total cAMP accumulated in 250 μL of this solution is quantitated using a commercially available low pH cAMP assay kit (Amersham BioSciences) by the procedure specified by the kit supplier. Any test subject showing cAMP accumulation in the same range as or higher than the positive control (buffer blank in the presence of α-MSH) is considered to be an agonist. A test subject showing accumulation in the same range as the negative control (buffer blank in the absence of α-MSH) is ineffective at the test concentration if the result is similar to the positive control where α-MSH is also present in the assay. A test subject showing accumulation in the same range as the negative control is considered to be an antagonist if there is inhibition in cAMP when α-MSH is present in the assay. Similar methods may be employed for MC3-R, using MC3-R cells. In a preferred embodiment, metallopeptides of this invention are ineffective at any concentration, and thus are neither an agonist nor an antagonist with respect to MC4-R.

In a particularly preferred embodiment, the metallopeptides of the invention are effective for treatment of sexual dysfunction but do not cause a biologically response associated with activation or inhibition of a melanocortin receptor, particularly MC3-R and/or MC4-R, and thus do not modulate feeding behavior in mammals or elicit or cause other responses characteristic of MC4-R specific molecules, including without limitation treatment of obesity or diabetes mellitus such as associated with MC3-R or MC4-R specific agonists, or treatment of cachexia or wasting disease associated with cancer, AIDS, failure to thrive syndrome, and diseases associated with aging and senility such as associated with MC4-R specific antagonists.

The invention is further illustrated by the following non-limiting examples.

EXAMPLE 1

Peptide Synthesis

Four peptides were synthesized by conventional peptide synthesis methods, heptanoyl-Ser(Bzl)-D-Phe(4-Cl)-Arg-Cys-NH$_2$, Ac-Nle-Ala-His-D-Phe-Arg-Gly-Cys-OH, Ac-Nle-Ala-His-D-Phe-Arg-Cys-OH, Ac-Nle-Ala-His-D-Phe-Arg-Cys-OH, and Ac-Nle-Ala-His-D-Phe-Cys-Arg-OH. The first three are thus representative of formula VI, while the fourth is representative of formula I. Thus heptanoyl-Ser(Bzl)-D-Phe(4-Cl)-Arg-Cys-NH$_2$ is illustrative of formula VI, wherein $R_1$ is H, $R_2$ is $CH_3$—$(CH_2)_5$, $R_3$ is an amino acid side chain moiety of Ser(Bzl), $R_4$ is an amino acid side chain moiety of D-Phe(4-Cl), $R_5$ is an amino acid side chain moiety of Arg and $R_6$ is NH$_2$, thereby providing the following metallopeptide on metal ion complexation:

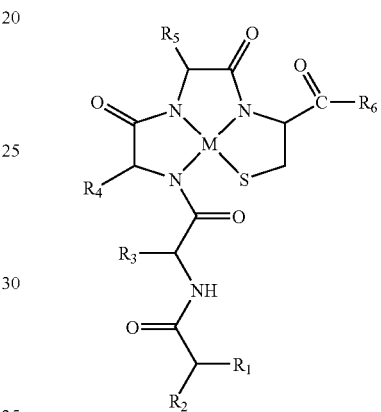

Similarly, Ac-Nle-Ala-His-D-Phe-Arg-Gly-Cys-OH is representative of formula VI, where n is 1 and $R_9$ is H.

EXAMPLE 2

Metallopeptide Formation

As a final step in solid phase peptide synthesis, the —SH group was selectively unprotected and rhenium metal ion complexed using the rhenium transfer agent Re(O)Cl$_3$(PPh$_3$)$_2$ in the presence of 1,8-Diazabicyclo[5,4,0]undec-7-ene (DBU) as base. In this manner, the metal-peptide complex was formed with the peptide chain still tethered to the solid support. The metallopeptide was then liberated from the solid support by treatment with trifluoroacetic acid (TFA) and purified.

Alternatively, the —SH containing peptide is librated from the solid-phase. It is then treated in methanol with the rhenium transfer agent Re(O)Cl$_3$(PPh$_3$)$_2$ in the presence of sodium acetate to complex the rheniumoxo group. The resulting metallopeptide is purified by RP-HPLC.

EXAMPLE 3

Metallopeptide Binding to Melanocortin Receptors

The metallopeptides of Example 1 complexed to a metal ion as in Example 2 were tested by means of competitive inhibition testing as described above, yielding the results set forth in Table 1:

TABLE 1

| Metal | | Percent Inhibition at 1 µM | | | |
|---|---|---|---|---|---|
| Ion | Sequence | MC1-R | MC3-R | MC4-R | MC5-R |
| ReO[V] | Heptanoyl-Ser(Bzl)-D-Phe(4-Cl)-Arg-Cys-NH$_2$ | 30 | 13 | 38 | 26 |
| ReO[V] | Ac-Nle-Ala-His-D-Phe-Arg-Gly-Cys-OH | 26 | 3 | 27 | 23 |
| ReO[V] | Ac-Nle-Ala-His-D-Phe-Arg-Cys-OH | 18 | 0 | 37 | 12 |
| ReO[V] | Ac-Nle-Ala-His-D-Phe-Cys-Arg-OH | 14 | 0 | 23 | 9 |

EXAMPLE 4

Metallopeptide Induction of Penile Erection

The ability of the metallopeptides of Example 1 complexed to rhenium as in Example 2 to induce penile erection in male rats was evaluated. Male Sprague-Dawley rats weighing 200-250 g were kept on a 12 hour on/off light cycle with food and water ad libitum. All behavioral studies were performed between 10 a.m. and 5 p.m. Groups of 4-8 rats were treated with peptides at a dose of 1 µg/kg body weight via intravenous administration. Immediately after administration, rats were placed into individual polystyrene cages (27 cm long, 16 cm wide, and 25 cm high) for behavioral observation. Rats were observed for 30 minutes and the number of yawns, grooming bouts and penile erections were recorded in three 10-minute bins. Each of the metallopeptides of Example 2 was observed to induce penile erections in male rats by intravenous injection, with a mean penile erection of between about 0.4 and 0.8 per rat.

EXAMPLE 5

Additional Metallopeptides

The following peptides are synthesized by conventional peptide synthesis methods as described and complexed with rhenium as in Example 2.

Heptanoyl-Cys-Ser(Bzl)-D-Phe(4-Cl)-Arg-NH$_2$
Aminoheptanoyl-Ser(Bzl)-D-Phe(4-Cl)-Arg-Cys-NH$_2$
Aminoheptanoyl-Ser(Bzl)-Cys-D-Phe(4-Cl)-Arg-NH$_2$
Aminoheptanoyl-Ser(Bzl)-D-Phe(4-Cl)-Cys-Arg-NH$_2$
Aminoheptanoyl-Ser(Bzl)-D-Phe(4-Cl)-Cys-OH
Hepatanoyl-Ala-His-D-Phe-Arg-Cys-OH
Hepatanoyl-Nle-Ala-His-D-Phe-Cys-Arg-OH The invention thus includes a metallopeptide forming a 6,5,5 ring structure. An illustration of formula VII is the peptide heptanoyl-Cys-Ser(Bzl)-D-Phe(4-Cl)-Arg-NH$_2$ wherein $R_1$ is H, $R_2$ is $CH_3$—$(CH_2)_5$, $R_3$ is an amino acid side chain moiety of Ser(Bzl), $R_4$ is an amino acid side chain moiety of D-Phe(4-Cl), $R_5$ is an amino acid side chain moiety of Arg and $R_6$ is NH$_2$, thereby providing the following metallopeptide on metal ion complexation:

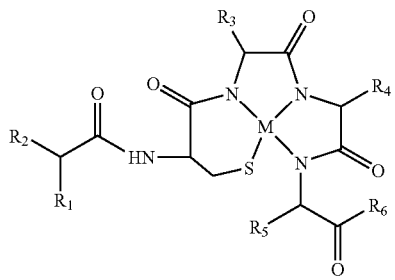

EXAMPLE 6

Change in food intake and body weight is evaluated for selected ICV-administered metallopeptides. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) were fed powdered chow and water ad libitum. For 1 week before treatment, 24-hour food intake and body weight change is recorded to assess a baseline for the group during vehicle treatment. The rats are dosed ICV with vehicle or selected compounds (1-3 nmol). The changes in body weight and food intake for the 24 hour period after dosing are determined. The changes in body weight and food intake for the 48 hour period, and in some cases the 72 hour period, after dosing is also measured to determine reversal of changes in body weight and food intake effect back to baseline.

EXAMPLE 7

Change in food intake and body weight is evaluated for selected IV-administered metallopeptides. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) were fed powdered chow and water ad libitum. For 1 week before treatment, 24-hour food intake and body weight change is recorded to assess a baseline for the group during vehicle treatment. The rats are dosed IV with vehicle or selected compounds (0.5-3 mg/kg). The changes in body weight and food intake for the 24 hour period after dosing were determined. The changes in body weight and food intake for the 48 hour period, and in some cases for the 72 hour period, after dosing is also measured to determine reversal of changes in body weight and food intake effect back to baseline.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

-continued

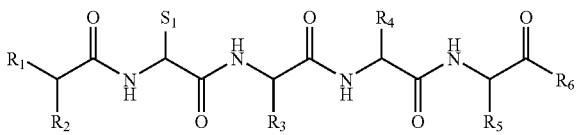

VII wherein:
$R_1$ is $NH_2$, $NH_3^+$, $NH_2$—$R_7$, $R_8$—$NH_2$ or H;
$R_2$ is H or a linear or branched $C_1$ to $C_{17}$ alkyl, aryl, heteroaryl, alkene, alkenyl, or aralkyl chain;
$R_3$ and $R_4$ are independently a $C_1$ to $C_6$ aliphatic linear or branched chain, including $CH_3$, or an aromatic amino acid side chain moiety, on the proviso that not more than one of $R_3$ and $R_4$ is a $C_1$ to $C_6$ aliphatic linear or branched chain;

What is claimed is:

1. A metallopeptide, consisting of a peptide of formula IV, V, VI or VII:

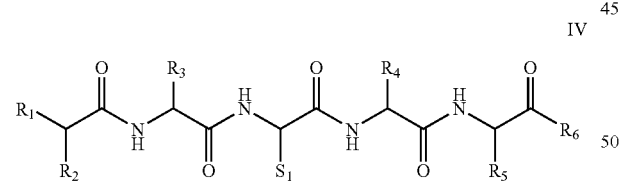

IV

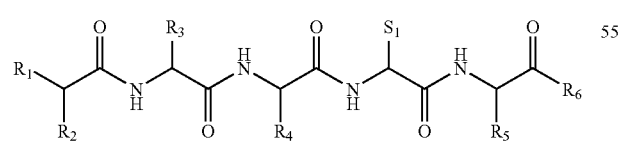

V

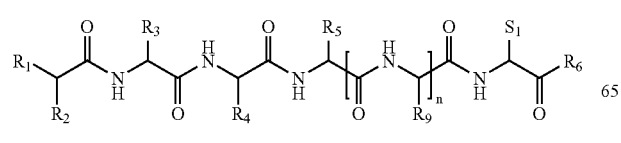

VI $R_5$ is a $C_1$ to $C_6$ linear or branched chain or a neutral hydrogen bonding or positively charged amino acid side chain moiety;
$R_6$ is OH or $NH_2$;
$R_7$ is from 1 to 3 amino acid residues, excluding residues with a side chain comprising indole, or a $C_1$-$C_{17}$ chain, including an alkyl, aryl, heteroaryl, alkene, alkenyl, or aralkyl, but excluding indole;
$R_8$ is an amino acid residue with an aliphatic side chain or its corresponding N-acylated derivative;
$R_9$ is H or $CH_3$;
$S_1$ is an amino acid side chain moiety including a sulfur atom (S) for metal ion complexation; and
the index value n is 0, in which case it is not present, or is 1; and
a metal ion complexed to S in $S_1$ and at least one preceding alpha amino nitrogen (N) atom, thereby displacing the hydrogen (H) in the alpha amino NH group.

2. The metallopeptide of claim 1, wherein $R_2$ is a $C_1$ to $C_{17}$ aliphatic linear or branched chain, an omega amino derivative of a $C_1$ to $C_{17}$ aliphatic linear or branched chain, or an acylated derivative of an omega amino derivative of a $C_1$ to $C_{17}$ aliphatic linear or branched chain.

3. The metallopeptide of claim 1 wherein the aromatic amino acid side chain moiety $R_3$ or $R_4$, or independently $R_3$ and $R_4$, is selected from the following:

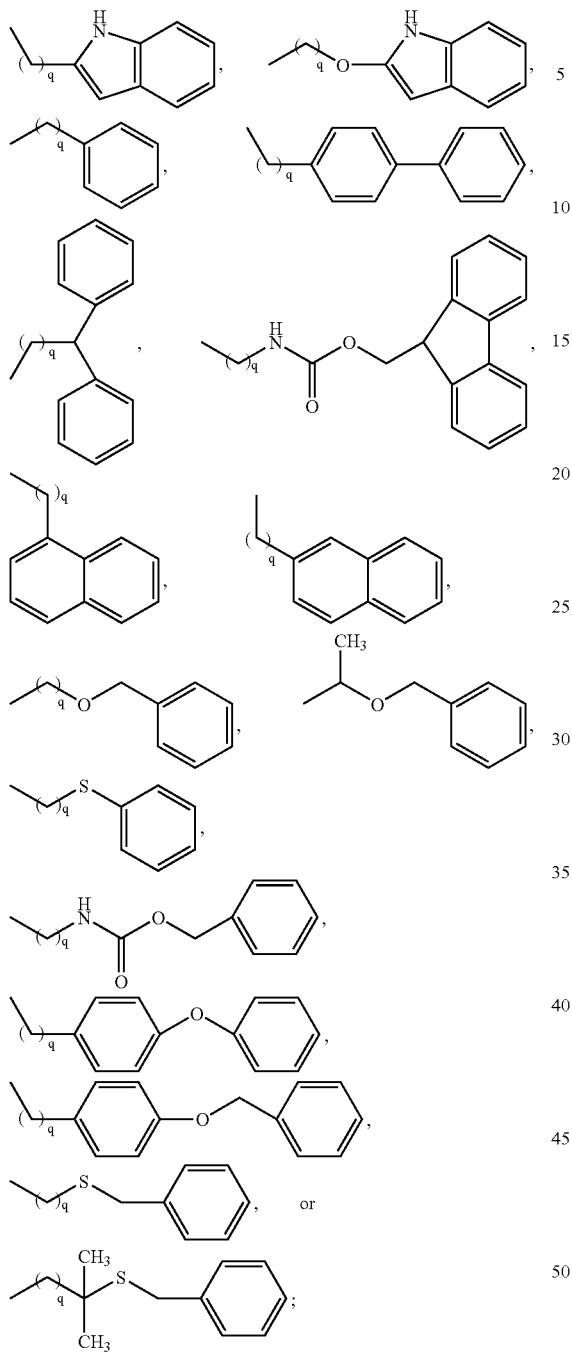

wherein q is from 0 to 5.

4. The metallopeptide of claim 3, wherein at least one aromatic ring comprising $R_3$ or $R_4$, or independently $R_3$ and $R_4$, is functionalized with one or more halogen, alkyl or aryl groups.

5. The metallopeptide of claim 1 wherein $R_5$ is an aliphatic or aromatic amino acid side chain moiety derived from a natural or synthetic L- or D-amino acid, wherein the moiety includes at least one nitrogen-containing group, selected from the groups consisting of an amide, imide, amine, guanidine, urea, urethane, or nitrile, but excluding indole.

6. The metallopeptide of claim 5 wherein $R_5$ is:

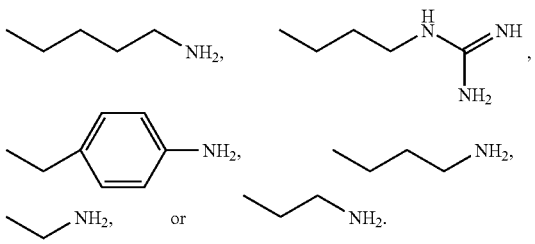

7. The metallopeptide of claim 1 wherein $R_5$ is a neutral hydrogen bonding amino acid side chain moiety selected from the group consisting of:

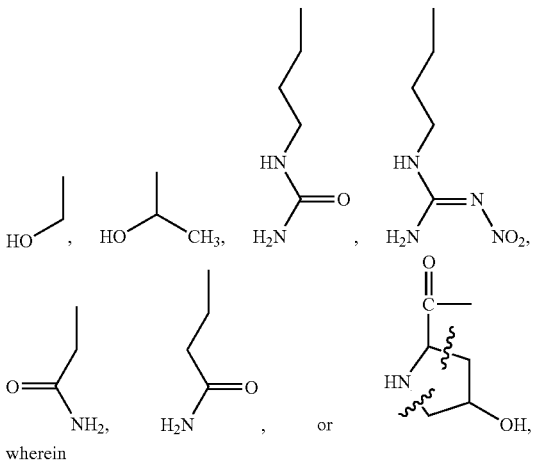

wherein

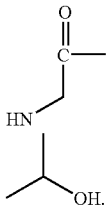

is a portion of the backbone, and $R_5$ is

8. The metallopeptide of claim 1 wherein $S_1$ is an amino acid side chain moiety selected from the group consisting of a side chain of L- or D-configurations of Cys, Pen and Hcys.

9. A method of treating erectile dysfunction in a male mammal, comprising administration of a therapeutically effective amount of a metallopeptide of claim 1 or a pharmaceutically acceptable salt thereof to a male mammal with erectile dysfunction, wherein the metallopeptide does not substantially bind any melanocortin receptor.

10. The method of claim 9, wherein the metallopeptide is further characterized in that it does not substantially affect energy homeostasis or feeding behavior when administered to a mammal in a therapeutically effective amount for treatment of erectile dysfunction.

11. The method of claim 9, further comprising administration of a therapeutically effective amount of a second erectile dysfunction pharmaceutical agent.

12. The method of claim 11 wherein the erectile sexual dysfunction pharmaceutical agent is an MC4-R agonist or a PDE-5 inhibitor.

* * * * *